United States Patent [19]
Caldwell et al.

[11] Patent Number: 5,667,799
[45] Date of Patent: Sep. 16, 1997

[54] METHOD FOR TREATING HEADACHE PAIN WITH TOPICAL LOCAL ANESTHETIC COMPOSITIONS

[76] Inventors: Larry J. Caldwell, 4146 Cranford Cir., San Jose, Calif. 95124; Bradley Stuart Galer, 7409 Woodlawn Ave. NE, Seattle, Wash. 98115

[21] Appl. No.: 558,598

[22] Filed: Oct. 30, 1995

[51] Int. Cl.$^6$ .......................... A61L 15/44; A61K 31/135
[52] U.S. Cl. ................................ 424/449; 514/817
[58] Field of Search ..................... 514/817; 424/449

[56] References Cited

U.S. PATENT DOCUMENTS

| | | | |
|---|---|---|---|
| 4,440,777 | 4/1984 | Zupan | 514/420 |
| 4,588,580 | 5/1986 | Gale et al. | 424/449 |
| 4,911,707 | 3/1990 | Heiber et al. | 424/449 |
| 4,963,591 | 10/1990 | Fourman et al. | 514/944 |
| 5,069,909 | 12/1991 | Sharma et al. | 424/449 |
| 5,070,084 | 12/1991 | Campbell | 514/248 |
| 5,330,452 | 7/1994 | Zook | 604/307 |
| 5,368,860 | 11/1994 | Sunami et al. | 424/448 |
| 5,401,728 | 3/1995 | Simon | 514/817 |

OTHER PUBLICATIONS

Kittrelle et al., "Cluster Headache—Local Anesthetic Abortive Agents", Arch Neurol (1985), 42:496–498.

*Primary Examiner*—Peter F. Kulkosky
*Attorney, Agent, or Firm*—Bret E. Field; Fish & Richardson P.C.

[57] ABSTRACT

Methods are provided for the treatment of a host suffering from head ache pain with topical applications of a local anesthetic. The topical local anesthetic composition comprises an effective amount of a local anesthetic in combination with eucalyptol as a penetration enhancing agent, and optionally an additional penetration enhancing agent. The topical local anesthetic composition is applied to a keratinized skin site proximal to target nerves associated with the headache pain, usually to the supraorbital or occipital regions of the head. Upon application of the topical composition, the local anesthetic rapidly penetrates the skin to block conduction in the target nerves and provide pain relief to the host.

10 Claims, No Drawings

METHOD FOR TREATING HEADACHE PAIN WITH TOPICAL LOCAL ANESTHETIC COMPOSITIONS

INTRODUCTION

1. Field of the Invention

The field of this invention is the treatment of headache pain.

2. Background

Headaches are a common problem affecting a large segment of the population. Headaches, such as tension type and migraine headaches, occur both intermittently and chronically, and can arise in response to variety of stimulants, including stress, injury, toxins in the environment and the like.

A variety of therapeutic agents have been developed for use in the treatment of patients suffering from headache pain. Some agents, such as aspirin, acetaminophen, vasoconstrictors and NSAIDs, e.g. ibuprofen and naprosyn, are administered systemically. Despite the prevalence of this form of treatment for headache pain, in some cases, systemic administration is not recommended. For example, oral administration of aspirin can result in stomach upset and patient discomfort. Furthermore, the agent can exert host systemic toxicity which may outweigh any therapeutic benefits provided by the agent. Finally, since the agent is administered systemically, its effects are also systemic, which may not be desired.

In view of the above problems and disadvantages associated with therapeutic agents that are administered systemically, regional administration of local anesthetics which selectively block conduction in target nerves is a desirable alternative for the treatment of headache pain. Use of local anesthetics is desirable because nerve conduction can be selectively blocked in only those nerves associated with the headache pain. Although use of local anesthetics in the treatment of headache pain is desirable, administration of an effective amount of the local anesthetic to the target nerves is difficult and/or inconvenient.

For example, a local anesthetic can be injected directly at the site of nerves associated with headache pain, e.g. the occipital and supraorbital nerves to effect a nerve block and thereby provide pain relief. See Garron, "Relieving Pain with Nerve Blocks," Geriatrics (1978) 33: 49–57. Although this method is effective in providing headache pain relief, because the local anesthetic is injected it must be administered by trained personnel. Furthermore, the patient must bear the discomfort associated with the injection of the local anesthetic.

Because of these disadvantages of administration by injection, the topical administration of local anesthetics is a desirable alternative mode of administration. However, local anesthetics by themselves do not readily penetrate the keratinized layer of the skin. See Review of Medical Pharmacology (Meyers et al. ed., 1978) pp. 217–226. Thus, intranasal application of local anesthetics has found use in the treatment of headache pain. See Brandt et al., "Cluster headache and chronic paroxysmal hemicrania: current therapy," Nervenarzt (1991) 62: 329–339.

For topical administration of local anesthetics to keratinized skin surfaces, additional measures must be taken to provide for penetration of the local anesthetic across the keratinized skin surface. One means of providing for penetration of the local anesthetic across the skin surface is to employ iontophoretic techniques, where an electric field is applied to the topical local anesthetic composition. The local anesthetic penetrates the keratinized skin surface under the influence of the applied electric field.

Another means of providing for penetration of keratinized skin is to employ formulations which promote local anesthetic penetration. Although such formulations are available and have been employed for a variety of applications, currently available topical local anesthetic formulations have not found widespread use for the treatment of headache pain. One reason that currently available formulations have not found widespread use for the treatment of headache pain is that an effective amount of the anesthetic agent does not penetrate the skin rapidly enough to provide pain relief in a sufficiently short period of time. For example, when EMLA (a eutectic mixture of lidocaine and prilocaine) is topically applied to a keratinized skin surface, it must be applied under an occlusive dressing for at least one hour before analgesia is experienced by the host. See Physician's Desk Reference, 1994, pp 544.

Thus, there is continued interest in the identification of topical local anesthetic formulations which are suitable for use in the treatment of headache pain. Such topical formulations should provide for rapid penetration of an effective amount of the local anesthetic through the skin surface, and thereby provide for rapid pain relief.

Relevant Literature

U.S. Pat. No. 4,440,777 describes topical applications comprising eucalyptol as an enhancing agent. Other patents of interest include U.S. Pat. Nos.: 4,588,580; 4,911,707; 5,069,909; 5,070,084; 5,330,452; and 5,368,860.

Kittrelle et al., "Cluster Headache. Local Anesthetic Abortive Agents," Arch. Neurol. (1985) 42: 496–498 reports the application of a 4% lidocaine solution to the sphenopalantine fossa in order to treat nitrate induced cluster headache pain.

SUMMARY OF THE INVENTION

Methods are provided for the treatment of a host suffering from headache pain with topical local anesthetic compositions. Topical local anesthetic compositions employed in the subject methods comprise an effective amount of a local anesthetic in combination with eucalyptol as a penetration enhancing agent. The local anesthetic compositions are applied to a keratinized skin site proximal to target nerves associated with the headache pain. Upon application, the local anesthetic rapidly penetrates the skin surface to reach, and block conduction in, the target nerves and provide for rapid pain relief.

DESCRIPTION OF THE SPECIFIC EMBODIMENTS

Methods are provided for the treatment of a host suffering from headache pain through application of topical local anesthetic compositions. The local anesthetic compositions employed in the subject methods comprise an effective amount of a local anesthetic in combination with eucalyptol as a penetration enhancing agent and provide for rapid penetration of the local anesthetic agent through a keratinized skin surface. In the subject methods, the local anesthetic composition is topically applied to a skin site proximal to target nerves associated with the headache pain. Upon application, the local anesthetic agent penetrates the skin to block conduction in the target nerves and provide pain relief to the host.

Topical compositions employed in the subject method will include a local anesthetic as the active agent. Although two or more local anesthetic agents may be present in the subject compositions, generally the subject compositions will comprise a single local anesthetic agent. The local anesthetic employed in the subject methods will be an anesthetic which, when administered in the topical formulations, rapidly penetrates a keratinized skin surface to block conduction in nerves underlying the skin surface. The local anesthetic will have a molecular weight and melting point that is compatible with transport across the keratinized skin surface. Generally, the molecular weight of the local anesthetic will not exceed about 300 dal, and will more usually not exceed about 250 dal. The melting point of the local anesthetic will be less than about 100° C. Generally, the local anesthetic will be a compound comprised of a secondary or tertiary amine linked through a connecting group to an aromatic group. The local anesthetic will be an alkanyl compound of from about 9 to 20 carbon atoms. Because the composition is applied topically, the local anesthetic will generally be present in the composition as a free base to promote penetration of the agent through the skin surface. A large number of local anesthetics are known in the art, many of which are suitable for topical application. Suitable local anesthetics include lidocaine, butamben, butanilicaine, ethyl aminobenzoate, fomocaine, hydroxyprocaine, isobutyl p-aminobenzoate, naepaine, octacaine, parethoxycaine, piridocaine, prilocaine, procaine, risocaine, tolycaine, trimecaine, particularly ethylaminobenzoate (benzocaine). The amount of local anesthetic present in the subject compositions will be sufficient to provide an effective amount of the agent when topically administered according to the subject methods. The precise amount of anesthetic agent present in the topical formulation will depend on the particular agent employed, but will generally range from 5 to 50% by weight, usually from about 10 to 40% by weight.

Critical to the topical applications employed in the subject methods is eucalyptol, which serves as a penetration enhancing agent for the local anesthetic. Eucalyptol (1,3,3-trimethyl-2-oxabicyclo[2,2,2]-octane) is the chief constituent of oil of eucalyptus and is also known as cineole and cajeputol. Eucalyptol is known in the art, having found use as an insect repellant and as a flavoring agent. The amount of eucalyptol present in the composition will range from about 10 to 80%, usually from about 10 to 50% by weight, and more usually from about 20 to 40% by weight of the composition.

Optionally, the subject composition may further comprise one or more additional penetration enhancing agents which work in combination with the eucalyptol to provide for rapid penetration of the local anesthetic. Additional penetration enhancing agents will be capable of rapid penetration of the skin and be pharmaceutically acceptable, i.e. non-toxic to the host at the levels at which they are present in the composition. Examples of additional penetration enhancing agents which may find use in the subject compositions include: propylene glycol and N-methyl-2-pyrrolidone. An additional penetration enhancing agent that finds particular use in combination with eucalyptol in the subject compositions is N,N-diethyl-m-toluamide (DEET). When present, the amount of this additional penetration enhancing agent in the subject compositions will vary depending on the particular agent, as well as the local anesthetic present in the composition. The amount of additional penetration enhancing agent or agents in the subject compositions will range from 10 to 80% by weight, usually from about 30 to 60% by weight. Generally, the ratio of eucalyptol to additional penetration enhancing agent in the subject compositions will be from 0.25:1 to 2:1, and will usually be from about 1:2 to 1:1.

The compositions comprising the local anesthetic, eucalyptol and any additional penetration enhancing agent employed in the subject methods will be formulated in a manner convenient for topical application. Thus, the subject compositions may be formulated as stable solutions or suspensions of the local anesthetic in eucalyptol. Alternatively, the local anesthetic and eucalyptol may be combined with one or more carrier materials to form a solution, suspension, gel, lotion, cream, ointment, aerosol spray or the like, as in known in the art.

Gel vehicles in which the subject local anesthetic and eucalyptol may be formulated to produce a topical application useful in the subject methods will physiologically acceptable and will generally comprise a solvent in combination with a thickening agent. The solvent will generally be an alkanol, such as an alcohol or polyol, including: ethanol, isopropanol, propylene glycol, glycerol, and the like. These alcohols and polyols may be used individually or in combination. In the gel vehicle, the solvent will generally be present in from about 1 to 80 weight %, more commonly 10 to 40 weight % of the topical composition.

Conventional gelling or thickening agents may be employed to provide for a formulation which can be conveniently applied to the skin. Gelling agents which have been found to be effective and are illustrative of conventionally used gelling agents for skin application include Carbomer 940 (neutralized with diisopropanolamine), neutralized polyacrylic acid, etc. The gelling agent will be used in an amount sufficient to provide the appropriate viscosity, generally being in the range of about 0.1–5 weight percent of the formulation.

Non-ionic surfactants may be included in the compositions, where the nonionic surfactants may serve as cosolvents and epidermal penetration enhancers, in addition to the eucalyptol and any optional penetration enhancing agent described above. Conventional surfactants may be employed, which are physiologically acceptable, such as sorbitan esters, etc. When present, the nonionic surfactant will generally be present in an amount of from about 2–20 weight percent of the formulation.

The topical composition may also contain other physiologically acceptable excipients or other minor additives, particularly associated with organoleptic properties, such as fragrances, dyes, emulsifiers, buffers, cooling agents (e.g. menthol), antibiotics, stabilizers or the like. The excipients and minor additives will be present in conventional amounts ranging from about 0.001% to 5%, more commonly 0.001–2%, by weight, usually not exceeding a total of 10% by weight.

Where convenient, e.g. with a gel formulation, the topical application may be covered with an occlusive dressing, which may be porous or non-porous, so as to protect the gel from mechanical removal during the period of treatment. Various inert coverings may be employed, which include the various materials which may find use in plasters, described below. Alternatively, non-woven or woven coverings may be employed, particularly elastomeric coverings, which allow for heat and vapor transport. These coverings allow for cooling of the pain site, which provides for greater comfort, while protecting the gel from mechanical removal.

Instead of a gel, a plaster may be employed, where the composition comprising the local anesthetic and eucalyptol, and any additional penetration enhancers, may be formulated into the adhesive of the plaster. In the case of plasters, the coverings may include polyvinyl chloride, polyvinylidene chloride, (SARAN®), polyethylene, synthetic rubber, woven or nonwoven polyester fabric, etc. The local anesthetic and the eucalyptol may be combined with the adhesive with the aid of a cosolvent, or a combination of cosolvents, such as propylene glycol, glycerin, methyl salicylate, glycol salicylate, or the like. The particular choice of adhesive is not critical, there being a wide variety of physiologically acceptable adhesives, which can maintain the local anesthetic, eucalyptol and any additional penetration enhancing agent, in contact with the skin.

Of particular interest are the topical local anesthetic compositions described in U.S. Pat. No. 4,440,777, the disclosure of which is herein incorporated by reference.

In the subject methods, the topical composition comprising the local anesthetic is applied to a keratinized skin site of the host proximal to target nerves associated with the headache pain. Nerves which are commonly associated with headache pain are the occipital and supraorbital nerves. The skin site at which the composition is applied will be sufficiently proximal to the target nerves, e.g. the skin site overlies the region innervated by the target nerves, so that upon contact of the composition with the skin surface, the local anesthetic can readily reach the target nerves and exert its anti-conduction activity. Of particular interest as skin sites of topical application are the supraorbital and occipital regions.

The subject compositions will be applied to the skin site for a period of time ranging from 0.25 to 6 hours, usually from about 0.5 to 5 hours, during which time the host will experience relief from pain due to the activity of the local anesthetic on the target nerves. If headache pain recurs following removal of the topical composition, a new topical composition may be applied. The process may be repeated as necessary and desired to achieve pain relief. Because of the nature of the topical local anesthetic composition employed in the subject methods, penetration of the local anesthetic is rapid. Therefore, the patient experiences relief from the pain shortly after application. Usually the patient will experience at least some relief from the headache pain about 0.25 to 30 min following application of the topical composition, usually about 0.5 to 30 min following application of the topical composition.

The amount of composition applied will usually be sufficient to cover a majority of the region of skin overlying the target nerves to ensure that conduction in a sufficient percentage of the target nerves is blocked, so that the host experiences pain relief. The exact amount of topical composition that is applied may be determined empirically. For example, where the topical application is applied to the supraorbital region of the head, the amount of composition applied will be sufficient to cover at least about 50%, more usually at least about 75% of the region. For solutions, dispersions, gels, lotions, creams and the like, the composition will be spread over the region and a covering optionally applied thereto. For patches, an appropriate sized patch will be placed over the region comprising the skin site.

Conveniently, the composition may be provided in a unit dosage format, which formats are known in the art.

Upon application of the topical composition, the local anesthetic rapidly penetrates the surface of the skin and blocks conduction of the target nerves which are proximal to the skin site. As a result, the patient will experience at least a partial subsidence in the intensity of headache pain, and in some cases may experience a complete cessation of pain. Thus, application of the topical local anesthetic compositions in accordance with the subject methods results in treatment of the host suffering from headache pain.

The following examples are offered by way of illustration and not by way of limitation.

EXPERIMENTAL

A mixture of DEET (N,N-diethyl-m-toluamide) and eucalyptol (1,3,3-trimethyl-2-oxabicyclo [2,2,2]-octane) was prepared in a ratio of 2:1. A sufficient amount of benzocaine free base (ca. 30% by weight) was dissolved in the mixture to produce a saturated solution of the local anesthetic.

The solution was topically applied to a female patient suffering from acute migraine without aura. The solution was applied directly to the areas of the patient's head where the supraorbital and occipital nerves are closest to the skin (the same area in which a needle would be inserted to perform regional anesthesia to these nerves). Prior to application of the solution, the patient rated her headache pain as "moderate" with "moderate" nausea and "moderate" light sensitivity.

After 15 minutes, the headache pain had subsided to a level described by the patient as "very mild." Furthermore, the patient reported no nausea or light sensitivity. In addition, the patient did not develop any noise sensitivity, which in the past had typically became sever during previous migraine attacks.

The patient's relief from the pain and other migraine symptoms lasted in excess of 2 hours. The patient was able to continue working following application of the topical local anesthetic solution. This was a favorable result compared to other forms of treatment which the patient had employed previously, where, despite treatment, the patient had to stop working.

It is evident from the above results and discussion that a novel and effective method of treating headache pain in a host is provided. The nature of the topical applications employed provides for rapid penetration of the skin surface by the local anesthetic. As a result, the patient experiences pain relief shortly after application of the composition. Furthermore, since the local anesthetic composition is topical, the method is convenient and tolerated well by patients.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a host suffering from headache pain by blocking conduction in occipital and supraorbital nerves associated with said headache pain, said method comprising:

applying at a keratinized skin site proximal to said target nerves in the supraorbital or occipital regions of the head of said host a topical local anesthetic composition comprising: an effective amount of local anesthetic wherein said local ansthetic is an amine linked through a connecting group to an aromatic group in combination with eucalyptol as a penetration enhancing agent;

whereby said local anesthetic rapidly penetrates the skin surface at said skin site to block conduction in said occipital or target nerves and said host experiences at least a partial subsidence in the intensity of said headache pain.

2. The method according to claim 1, wherein said topical local anesthetic composition further comprises an additional penetration enhancing agent.

3. A method for treating a host suffering from headache pain by blocking conduction in target nerves associated with said headache pain, said method comprising:

applying at a keratinized skin site proximal to said target nerves a topical local anesthetic composition comprising: (a) an effective amount of a local anesthetic, wherein said local anesthetic is an amine linked through a connecting group to an aromatic group; (b) eucalyptol as a penetration enhancing agent and (c) an additional penetration enhancing agent, wherein said target nerves are selected from the group consisting of occipital and supraorbital nerves;

whereby said local anesthetic rapidly penetrates the skin at said skin site to block conduction in said target nerves and said host experiences at least a partial subsidence in the intensity of said headache pain.

4. The method according to claim 3, wherein said additional penetration enhancing agent is N,N-diethyl-m-toluamide.

5. A method for treating a host suffering from headache pain by blocking conduction in target nerves selected from the group consisting of the occipital and supraorbital nerves, said method comprising:

applying at a keratinized skin site proximal to said target nerves a topical local anesthetic composition comprising: (a) an effective amount of benzocaine, (b) eucalyptol and (c) N,N-diethyl-m-toluamide;

whereby said benzocaine rapidly penetrates the skin at said skin site to block conduction in said target nerves and said host experiences at least a partial subsidence in the intensity of said headache pain.

6. The method according to claim 4, wherein said benzocaine is present in said composition in amount ranging from 20 to 40% by weight.

7. The method according to claim 4, wherein the ratio of said eucalyptol to N,N-diethyl-m-toluamide in said composition is 1:2.

8. The method according to claim 4, wherein said composition is formulated as a gel.

9. The method according to claim 8, wherein said gel is covered with a dressing.

10. The method according to claim 4, wherein said composition is formulated into the adhesive of a plaster.

* * * * *